(12) United States Patent
Bertini et al.

(10) Patent No.: US 7,772,430 B2
(45) Date of Patent: Aug. 10, 2010

(54) DERIVATIVES OF ARYLSULFONAMIDO-SUBSTITUTED HYDROXAMIC ACID AS MATRIX METALLOPROTEINASES INHIBITORS

(75) Inventors: Ivano Bertini, Florence (IT); Marco Fragai, Arezzo (IT); Mauro Lo Conte, Pistoia (IT); Claudio Luchinat, Florence (IT); Cristina Nativi, Florence (IT); Chiara Venturi, S. Macario Monte (IT)

(73) Assignee: Protera S.R.L., Sesto Fiorentino (IT)

( * ) Notice: Subject to any disclaimer, the term of this patent is extended or adjusted under 35 U.S.C. 154(b) by 237 days.

(21) Appl. No.: 11/659,431

(22) PCT Filed: Jul. 29, 2005

(86) PCT No.: PCT/EP2005/053722

§ 371 (c)(1), (2), (4) Date: Feb. 5, 2007

(87) PCT Pub. No.: WO2006/013193

PCT Pub. Date: Feb. 9, 2006

(65) Prior Publication Data

US 2008/0249032 A1 Oct. 9, 2008

(30) Foreign Application Priority Data

Aug. 3, 2004 (IT) ............ FI2004A0174

(51) Int. Cl.
C07C 303/00 (2006.01)
C07C 307/00 (2006.01)
C07C 309/00 (2006.01)
C07C 311/00 (2006.01)
A01N 41/06 (2006.01)
A61K 31/18 (2006.01)
A61K 31/70 (2006.01)
A01N 43/04 (2006.01)
C07H 15/00 (2006.01)
C07H 17/00 (2006.01)
C07H 17/02 (2006.01)

(52) U.S. Cl. ............ 564/89; 514/604; 514/25; 536/17.6

(58) Field of Classification Search .......... 564/89; 514/604, 25; 536/17.6

See application file for complete search history.

(56) References Cited

U.S. PATENT DOCUMENTS 6,114,568 A * 9/2000 Andresen et al. .......... 560/12

FOREIGN PATENT DOCUMENTS

| EP | 0606046 A1 | 7/1994 |
|---|---|---|
| EP | 0935963 A2 | 8/1999 |
| WO | WO9817645 | 4/1998 |
| WO | WO9833768 | 8/1998 |
| WO | WO9850348 | 11/1998 |
| WO | WO9906340 | 2/1999 |

OTHER PUBLICATIONS

Wolff et al., Burger's Medicinal Chemistry and Drug Discovery (1994) Wiley-Interscience, Fifth Edition, vol. I: Principles and Practice, pp. 975-977.*

Prakash Rao, H.S. (2003) Capping Drugs: Development of Prodrugs. Resonance, p. 19-27.*

Scozzafava et al., "Protease Inhibitors: Synthesis of Potent Bacterial Collagenase and Matrix Metalloproteinase Inhibitors Incorporating N-4-Nitrobenzylsulfonylglycine Hydroxamate Moieties," J. Med. Chem., 2000, 43, 1858-1865.

Whittaker et al., "Design and Therapeutic Application of Matrix Metalloproteinase Inhibitors," Chem. Rev. 1999, 99, 2735-2776.

Kumar et al., "A Quantitative Structure-Activity Relationship Study on Some Matrix Metalloproteinase and Collagenase Inhibitors," Bioorganic & Medicinal Chemistry 11, 2003, 421-426.

Scozzafava et al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N-Hydroxysulfonamides Inhibit Both These Zinc Enzymes," J. Med. Chem., 2000, 43, 3677-3687.

\* cited by examiner

*Primary Examiner*—Leigh C Maier
*Assistant Examiner*—Scarlett Goon
(74) *Attorney, Agent, or Firm*—Abelman, Frayne & Schwab

(57) ABSTRACT

Described herein are derivatives of arylsulfonamido-substituted hydroxamic acid of formula (I) having good solubility in water and inhibitory activity of matrix metalloproteinases, useful for the preparation of pharmaceutical compositions for the treatment of diseases associated to a pathologic activity and/or an over-expression of metalloproteinases, and of cosmetic preparations having anti-ageing properties in particular for hair and skin.

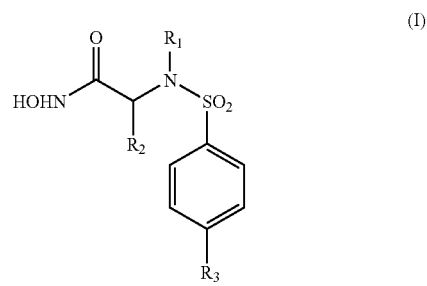

(I)

6 Claims, No Drawings

DERIVATIVES OF ARYLSULFONAMIDO-SUBSTITUTED HYDROXAMIC ACID AS MATRIX METALLOPROTEINASES INHIBITORS

FIELD OF INVENTION

The invention relates to the field of compounds that are inhibitors of proteinase, in particular of compounds of formula (I) reported hereinafter, having good solubility in water and inhibitory activity of matrix metalloproteinase, useful for the treatment of diseases associated to pathologic activity and/or overexpression of the above said enzymes, as well as for anti-ageing cosmetic treatments.

STATE OF ART

Matrix metalloproteinases (MMP) are a family of more than 20 different Zn-dependent enzymes, responsible for degradation of extra cellular matrix.

The cellular matrix components carry out a fundamental role in modulating the cellular environment during the development, the morphogenesis and the tissue repair processes. Therefore, their activity is finely regulated, in regard to trascriptase as well as activation and also by action of endogenous inhibitors such as TIMP (Tissue Inhibitors of MetalloProteinases) and $\alpha_2$-macroglobulin.

An alteration of the delicate equilibrium which regulates the activity of MMP's is connected to insurgence and progression of numerous pathologies such as pulmonary emphysema, rheumatoid arthritis, osteoarthritis, diabetic retinopathy, photoaging of epidermis and some kinds of tumour.

Besides the above said endogenous inhibitors, many different compounds developed as synthetic inhibitors of MMP can be found in the literature. A group of inhibitors mentioned in many publications is that of compounds containing the functional group hydroxamic (—CO—NH—OH), such as the derivatives arylsulfonamido-substituted hydroxamic acid described in European Patents No. 606 046 and No. 766 672.

Most of these synthetic inhibitors are not very selective, because they are able to inhibit not only one, but several MMP's. The derivatives of arylsulfonamido-substituted hydroxamic acid mentioned above, for example, are described in the European Patents No. 606 046 and No. 766 672 as inhibitors of MMP in general, and in particular as inhibitors of stromelysin (MMP-3), gelatinase (MMP-2) e collagenase I (MMP-1).

Despite their inhibitory activity, the lack of selectivity observed for these compounds seems to be the cause of muscle-skeletal pains appearing collateral effect following to the administration of these compounds. Moreover, different therapeutic approaches showed that the active principle with optimal therapeutic results, is the one who inhibits selectively the MMP whose pathological activity is connected to a certain disease, but does not inhibit any other MMP to the same extent.

It is therefore still felt providing selective synthetic inhibitors, in particular inhibitors of some metalloproteinases for which only wide spectrum inhibitors are now available. A particular case is that of metalloelastase from macrophage (MMP-12), an enzyme that is particularly active in the degradation of elastin and of the components of basal membrane like fibronectin, laminin, entactin, proteoglycans and collagen IV. Many studies have shown that there is a direct relation between the overexpression of MMP-12 and the development and progression of pulmonary emphysema (*Science* 1997, 277, 2002-4).

Cigarette smoke and inhalation of other harmful substances, related to professional activities, favour infiltration of macrophages and induce to overexpression of metalloelastase; so that they are among the major factors of risk for the development and progression of pulmonary emphysema. The role of the MMP-12 in pulmonary emphysema is therefore ascertained. Even if there is a big therapeutic potential for this discovery—millions of people all over the world are affected from this pathology—there is still not available a selective inhibitor of MMP-12, but only wide spectrum inhibitors are known, such as batimastat and marimastat, that work on activity of this enzyme as well as on activity of several other metalloproteinases. Indeed they are reported to exhibit $IC_{50}$ values of about 3 to about 16 nM against each of MMP-1, MMP-2, MMP-7, MMP-9 and MMP-12 (Whittaker, *Chem. Rev.* 1999, 99, 2735-2776).

Also the derivatives of arylsulfonamido-substituted hydroxamic acid disclosed in European Patent No. 766 672 are mentioned as synthetic inhibitors of MMP-12, and they are reported to exhibit $IC_{50}$ values of about 1 to about 10 nM; but also in this case the compounds show inhibitory activity also against other metalloproteinases.

Moreover, the lack of selectivity is generally a factor of limitation in therapeutic treatment, and it would be an advantage to have available a principle that is active only against a particular pathology and suitable to be formulated for the particular treatment of this pathology.

At this aim it is important to note that the synthetic inhibitors described in the European Patents No. 606 046 and No. 766 672 generally have scarce solubility in water, which limits its use and may also limit bioavailability of the active principle. In view of what reported above, the need of novel synthetic inhibitors of MMP's, having good solubility in water, selective inhibitory activity against specific MMPs and lower inhibitory activity against other MMPs, is therefore felt.

SUMMARY OF THE INVENTION

Now the Applicant has found that the compounds of formula (I) hereinafter reported, besides having a good solubility in water, inhibit selectively the enzymatic activity of matrix metalloproteinases MMP-12, MMP-8 and MMP-13, whereas they inhibit for example the MMP-7 to a much lower extent.

The present compounds are therefore particularly useful for the treatment of all kinds of diseases associated to a pathological activity and/or overexpression of MMP-12, for example the treatment of pulmonary emphysema, and for the treatment of periodontitis and other diseases associated to a pathological activity and/or overexpression of MMP-8 and MMP-13.

Subject of the present invention are therefore the compounds of formula (I)

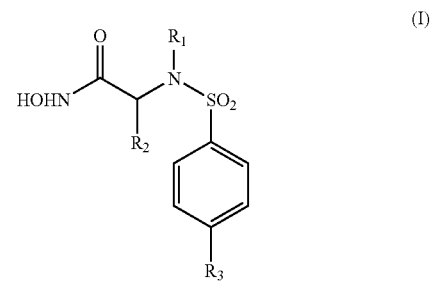

wherein

R$_1$ is an alkyl group substituted with one or more substituents selected from the consisting group of OH, SH, NH$_2$, NHR', X-glucide, X-glycoaminoacid and X-glycopeptide, wherein R' is selected from the group consisting of lower alkyl possibly substituted with one or more hydroxyl groups, aryl, aryl-alkyl, X-glucide, X-glycoaminoacid, X-glycopeptide and lateral chains of amino acids, and X is a divalent spacer group comprising atoms selected from O, S, N and C, provided that R$_1$ comprises at least two groups OH, R$_2$ is selected from the group consisting of H, alkyl possibly substituted with one or more hydroxyl, aryl and lateral chains of amino acids, R$_3$ is selected from the group consisting of H, OH, alkyl, aryl, oxoalkyl, and oxoaryl, and their prodrugs and pharmaceutically acceptable salts thereof.

Further subject of the invention are the pharmaceutical compositions comprising as active principle at least a compound of formula (I) as defined above; the use of these compounds for the preparation of pharmaceutical compositions useful for the treatment of diseases associated to the pathological activity and/or overexpression of matrix metalloproteinases and the process of preparation of compounds with formula (I).

The above said compounds of formula (I) also showed a certain ability of inhibiting the enzymatic activity of matrix metalloproteinases MMP-1, to an extent satisfactory for the cosmetic use of those compounds (I) as anti-ageing products.

Further subject of the invention are therefore cosmetic preparations comprising at least a compound of formula (I) as defined above; the use of these compounds as an active ingredient for the preparation of cosmetic preparations, to cosmetically treat or prevent the phenomena of cutaneous and hair ageing and/or to improve their appearance, as well as the method of cosmetic treatment of skin and/or hair, comprising the step of applying, to the surface of the skin and/or the hair, a cosmetically effective amount of at least a compound of formula (I) as defined above or of a cosmetic preparation thereof.

Further subject of the invention is the compound of formula (I), wherein R$_1$ is H, R$_2$ is hydroxymethyl and R$_3$ is methoxy, or its prodrugs or pharmaceutically acceptable salts thereof; the pharmaceutical compositions comprising this compound and its use for the preparation of pharmaceutical compositions for the treatment of diseases associated to pathologic activity of matrix metalloproteinases.

Features and advantages of the invention will be illustrated in detail in the following description.

DETAILED DESCRIPTION OF THE INVENTION

Preferred compounds of formula (I) according to the invention are the compounds wherein R$_1$ is a group of formula (II)

(II)

wherein R$_4$ is selected from among X-glucide, X-glycoaminoacid and X-glycopeptide wherein X is as defined above; or R$_4$ is a group of formula (III)

(III)

wherein

R$_6$ is selected from the group consisting of OH, SH, NH$_2$, lower alkyl, X-glucide, X-glycoaminoacid and X-glycopeptide wherein X is as defined above;

R$_5$ is selected from the group consisting of H, OH, alkyl, and alkyl substituted with one or more groups OH; and n=0, 1, 2, provided that, when R$_4$ is a group of formula (III), the total number of hydroxyl groups contained in R$_5$ and R$_6$ is at least two.

According to the present invention the definition of X as "a divalent spacer group comprising atoms selected from O, S, N, C" includes, for example, —O—, —S—, —NH—, —NR'— wherein R' is as defined above, C1-C8 alkylene, or combinations of said alkylene with said heterofunction O, NH, NR', S, the latter bonding to the carbon skeleton of the glucide, glycoaminoacid or glycopeptide residue.

According to the present invention by the term "prodrug" it is meant a derivative of compound of formula (I) derivatized so as to be converted in the corresponding compound (I) under physiological conditions; whereas the expression "pharmaceutically acceptable salts" means the addition salts of one of the functional groups of the molecule with mineral acids or organic acids, such as hydrochlorides, or with basic salts, such as ammonium salts, and alkali or alkaline-earth metals salts.

If it is not otherwise specified, the terms "alkyl", "lower alkyl", "oxoalkyl", "aryl", "oxoaryl", "aryl-alkyl", and "lateral chains of amino acids", as used in the present invention, should be meant as follows:

the term "alkyl" relates to hydrocarburic chains, linear or branched, having only single bonds, and preferably this term relates to C1-C20 chains. Examples of alkyl groups according to the invention include, but are not limited to, methyl, ethyl, propyl, iso-propyl, n-butyl, iso-butyl, tert-butyl, pentyl, iso-pentyl, neo-pentyl, tert-pentyl;

the term "lower alkyl" relates to an alkyl, linear or branched, having from 1 to 7 carbon atoms, preferably from 1 to 4 carbon atoms;

the term "oxoalkyl" indicates a group —O-alkyl, wherein "alkyl" is defined as above. Examples include, but are not limited to, methoxy, ethoxy, propoxy and isopropoxy;

the term "aryl" relates to a carbocyclic or heterocyclic group with one or more unsaturated rings, each ring having from 5 to 8 members, and preferably 5 or 6 members. Examples of aryl groups according to the invention include, but are not limited to, benzyl, phenyl, piridyl, toluoyl, naphtyl;

the term "oxoaryl" indicates a substituent —O-aryl, where "aryl" is as defined above;

the term "arylalkyl" indicates a group having an alkyl and an aryl substituent as above defined. As example, arylalkyl includes but is not limited to ethylphenyl, isobutylphenyl, benzyl, ethylbenzyl, propylbenzyl, isopropylbenzyl, butylbenzyl, isobutylbenzyl, cycloexylbenzyl, stirenyl and biphenyl;

- the term "lateral chains of amino acids" relates to the lateral chains of L or D natural alfa aminoacids or the lateral chains of rare or not natural aminoacids, and preferably of aminoacids selected from serine, threonine, cysteine, lysine, asparagine, leucine, tyrosine, tryptophan and histidine;
- the term "glucide" relates to α or β saccharide residues, and in particular to mono-, di- and oligosaccharides. Examples of glucides according to the invention include, but are not limited to, glucose, galactose, lactose, N-acetylglucose, fructose and fucose, and preferably glucose. Preferred residues X-glucide thus are O-saccharide, O-glycoside, alkylene-O-saccharide or alkylene-O-glycoside, especially wherein the glycoside residue is the one of glucose.
- the term "glycoaminoacid" or "glycopeptide" relates to saccharide residues α or β, respectively bound to one or more aminoacids, typically up to a maximum of 4, at the anomeric position or another position, and bound to sulfonamidic nitrogen of the base structure, through the saccharidic portion or the peptidic portion. Examples of "glycoaminoacids" or "glycopeptides" according to the invention include, but are not limited to, seryl-O-glucopyranosides and cysteyl-S-glucopyranosides.

According to the invention the groups alkyl, oxoalkyl, aryl and oxoaryl may be possibly substituted, for example with groups of OH, $NH_2$ and halogen.

According to a preferred embodiment of the invention $R_3$ is selected from phenyl and methoxy; more preferably $R_3$ is methoxy.

If it is not otherwise specified, the present compounds of formula (I) may have (R) or (S) absolute configuration of chiral centre; mixtures of the two configurations (R) and (S) in any ratio are within the scope of the present invention. Any possible geometric isomers, optical isomers, racemate or mixtures thereof, are to be considered within the scope of the invention too.

Compounds of formula (I) described above, can be prepared starting from suitable aminoacids and arylsulfonic derivatives, for example by a process comprising the following steps:

i) condensation of amino acid of formula (IV), previously esterified, with the chloride of arylsulfonic acid of formula (V), in an organic solvent and in the presence of a base, to obtain the corresponding arylsulfonic derivative of formula (VI):

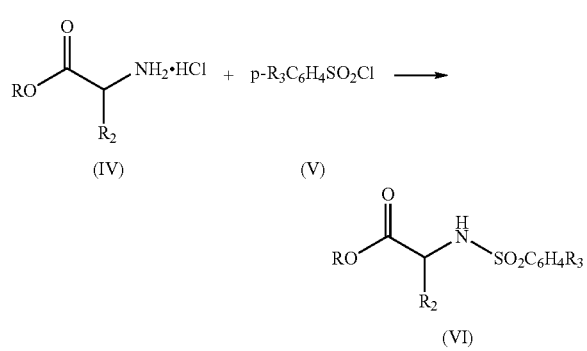

wherein $R_2$ and $R_3$ are as defined above, and R is lower alkyl, preferably methyl;

ii) reaction of compound of formula (VI) coming from step i) with a suitable reactive derivative of formula XR', suitable for introducing the group $R_1$ or a precursor thereof, to obtain the compound of formula (VII)

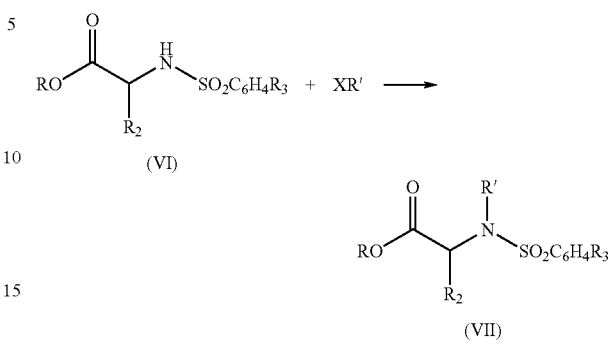

wherein R, $R_2$ and $R_3$ are as defined above, X is chosen from —OH and halogen, such as chloro, bromo or iodo, and R' is the group $R_1$ as defined above, or a precursor thereof that may give the group $R_1$ by hydrolysis.

iii) possible hydrolysis of compound of formula (VII) coming from step ii) to obtain the compound of formula (VIII)

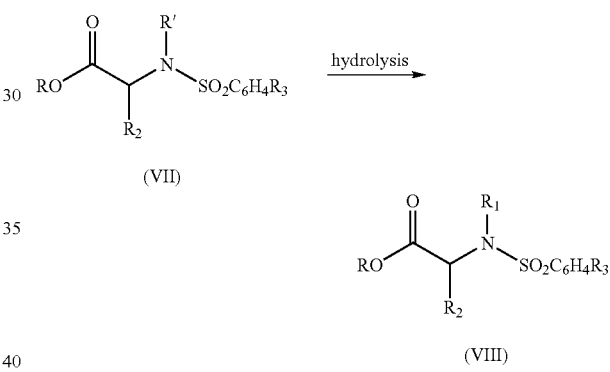

wherein R, R', $R_1$, $R_2$ and $R_3$ are as defined above;

iv) reaction of the ester of formula (VIII) coming from step iii) with hydroxylamine to give the corresponding N-hydroxyamide of formula (I)

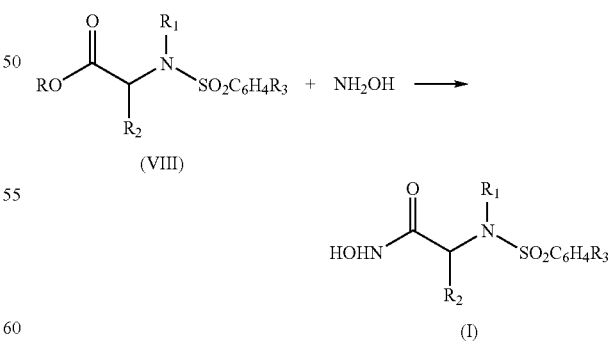

wherein R, $R_1$, $R_2$ and $R_3$ are as defined above.

The starting compounds of the process described above, are commercially available products, or can be prepared with processes well known in the art starting from commercially available products.

When the compounds of formula (I) wherein $R_1$ is X-glucide are desired, a glycosylation is carried out in step ii) of the process described above; for example, this reaction may be carried out using a suitable peracetylated glycosyl bromide as the reactive derivative XR' and silver triflate as catalyst, or using the suitable glycosyl trichloroacetimidate, according to the Schmidt glycosylation procedure.

The present compounds of formula (I), as such or as pro-drugs or pharmaceutically acceptable salts thereof, can be used for the preparation of pharmaceutical compositions according to conventional methods of preparation in the pharmaceutical field.

These pharmaceutical compositions can be formulated in conventional manner, and may comprise one or more pharmaceutically acceptable excipients and/or diluents.

Administration of these compositions may be accomplished in any conventional way, for example by parental way, in form of injectable solutions, by oral, topical, nasal, etc., even though the preferred way is inhalation via aerosol because the present pharmaceutical compositions are particularly useful for treatment of pulmonary emphysema and administration via aerosol assures pulmonary concentrations of the active principles absolutely superior than via oral administration.

Pharmaceutical formulations of the compounds of general formula (I) according to the invention may include, besides aerosol, also tablets, capsules, pills, solutions, dispersions, suspensions, liposomal formulations, microspheres, nano-spheres, creams, unguents, and emulsions, and can also be prepared in order to achieve a controlled or delayed release of the active principle.

These pharmaceutical compositions can comprise at least one amongst the present compounds of formula (I) as active principle, possibly in combination with other active principles or adjuvants, selected according to the pathologic conditions to be treated.

The present pharmaceutical compositions comprising the compounds of the invention are suitable for the pharmacological treatment of pathologic conditions associated to an increased activity of metalloproteinases, in particular of metalloelastase MMP-12, and are therefore particularly useful for the treatment of pulmonary emphysema.

The compound of formula (I) wherein $R_1$ is H, $R_2$ is $CH_2OH$ and $R_3$ is $OCH_3$, that is 2-[4-methoxy-benzenesulfo-nylamino]-3,N-dihydroxy-propionamide, is further subject of the invention, such as the pharmaceutical compositions comprising it as active principle, and its use for the treatment of pathologic conditions associated to an increased activity of metalloproteinases, in particular of MMP-12. This compound can be prepared with a process analogue to that described above for the preparation of compounds of formula (I), but wherein the compound of formula (VI) coming from step i) is directly reacted with hydroxylamine as in step iv).

The present compounds of formula (I) as described above, are also endowed with anti-ageing properties which make them suitable for use in cosmetic formulations.

The cosmetic formulations may exist in a wide variety of preparations, for example: creams, gels, lotions, alcoholic and aqueous/alcoholic solutions, emulsions, wax/fat compositions, stick preparations such as lipsticks or deodorants, powders or ointments.

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

Of special importance as preparations for the skin are daily care and/or anti-ageing preparations, including light-protective preparations, such as sun milks, lotions, creams, oils, sunblocks, pretanning preparations or after-sun preparations, also skin-tanning preparations, for example self-tanning creams, skin whitener preparations, skin lightener preparations or combinations of such systems. Of particular interest are sun protection creams, sun protection lotions, sun protection milk and sun protection preparations in the form of a spray.

Of special importance as preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyl-dodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$-carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyidodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants alpha glucosylrutin (CAS No. 130603-71-3), 2-butyloctyl o-hydroxybenzoate (CAS No. 190085-41-7), vitamin E (CAS No. 1406-18-4), vitamin E acetate (CAS No. 58-95-7), diethylhexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or imino-disuccinic acid and imiondisuccinic acid salts [CAS 7408-20-0] or latex particles, aloe vera, chamomile, ginko biloba, ginseng, coenzyme Q10, *laminaria ochroleuca* extract, *magnolia oborata* extract, *melalenca alternifolia* leaf oil, *rubus idaeus* seed oil, *vaccinium macrocarpon* seed oil, pumpkin seed extract, pumpkin seed oil, grape seed extract, carnosine, alpha-arbutin, madecassoside, termino-laside, tetrahydrocurcuminoids (THC), mycosporines, mycosporine like amino acids from the red alga *porphyra umbilicalis*, mycosporine-like amino acids (as described in WO 2002/039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO 03/41675 and linear poly-alpha-glucans as described in U.S. Pat. No. 6,616,935.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, *macadamia* nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in *Cosm. Toil.* 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate.

Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block (oxyethylene). Zwitterionic surfactants that carry at least one quaternary ammonium group and at least one carboxylate and/or sulfonate group in the molecule. Zwitterionic surfactants that are especially suitable are betaines, such as N-alkyl- N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251. Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-[Tefose 2000], PEG-6 stearate and ceteth-20 and glyceryl stearate and steareth-20 [Tefose 2561], glyceryl stearate and ceteareth-20 [Teginacid H, C, X]. Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide. The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic preparations, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colorants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Rheology Modifiers

Viscosity additives set up network structures throughout the base fluid, and exhibit the "yield value". Clay and polymer additives possess high yield values, and are therefore used to positively support suspension problems. Regarding particle suspension, the addition of such viscosity building agents will help to decrease the density difference between the particle and the fluid media surrounding, and therefore will lead to better resistance to the settling down of the particles.

Thickeners can be divided into at least 2 general categories: those that show the best performance in water, and those that show the best performance in oils.

In addition, it is also possible to differentiate them according to their nature, for example synthetic polymers, natural polymers and their derivatives, mineral polymers etc., but also according to their ionic character such as anionic, cationic, nonionic or amphoteric.

TABLE 1

Natural thickeners
Most of them are derived from the Polysaccharides category

| | |
|---|---|
| RM 1 | Cellulose gum such as cross-linked or not Sodium Carboxymethylcellulose or even Cocodimonium Hydroxypropyloxyethyl Cellulose |
| RM 2 | Microcrystalline cellulose and Carboxymethyl Cellulose Sodium |
| RM 3 | Guar gum and derivatives (except hydroxypropyl-modified), - Biosacccharide gum-1 (Fucogel 1000 from Solabia), -Sclerotium Gum (Amigel from Alban Muller) or Scleroglucan (Tinocare GL from Ciba SC) |
| RM 4 | Galactoarabinan from Larch extract (Laracare A200) |
| RM 5 | Acaccia/Arabic Gum |
| RM 6 | Konjac mannan; linear chains of glucose and mannose units linked in (β-1,4) |
| RM 7 | Pectin polysaccharides; backbone of galacturonic acid and rhamnose with side chains as Rhamnogalacturonan I or Rhamnogalacturonan II |
| RM 8 | Xanthan Gum; (β-1,4) linked Glucose residues or Dehydroxanthan Gum (Amaze XT from National Starch) |
| RM 9 | Starch and derivatives: Potato starch modified (Structure Solanace from National Starch); Hydroxypropyl Starch Phosphate (Structure XL or ZEA |

TABLE 1-continued

Natural thickeners
Most of them are derived from the Polysaccharides category

|  | |
|---|---|
|  | from National Starch); Amylose and Amylopectin polymeric forms; Maltodextrins |
| RM 10 | Carrageenan from red algae as Sulfated linear polysaccharides |
| RM 11 | Alginic acid and alginates from brown algae; polymers of mannuronic acid and Guluronic acid |

TABLE 2

Mineral thickeners
Most of them are derived from smectite clays and silica derivatives

| | |
|---|---|
| RM 12 | Aluminum Silicates or Bentonites or Montmorillonites such as Magnesium Aluminum Silicates (Veegum range from R. T. Vanderbilt) and Quaternized compounds such as Stearalkonium Bentonite |
| RM 13 | Magnesium Silicates or Hectorites such as Bentone Series (from Elementis Specialties) and Quaternized compounds such as Disteardimonium Hectorite (to disperse in lipophilic media) |
| RM 14 | Magnesium sodium Fluorosilicate or modified Mica |
| RM 15 | Synthetic layered Silicates; similar structure to Hectorites; Sodium Magnesium Silicates (Laponite range from Solvay) |
| RM 16 | Fumed Silicas such as Aerosil range from Degussa |

TABLE 3

Synthetic Rheology modifiers
Poly(acrylic acid) PAA and its copolymers; within such structure, it can be incorporated ester groups, with hydrophilic character such as 2-Hydroxyethyl Methacrylate etc.

| | |
|---|---|
| RM 17 | Carbomer or crosslinked polyacrylic acid polymer such as Carbopol Ultrez 10, Carbopol ETD2001, Carbopol ETD2050 from Noveon Inc |
| RM 18 | Sodium polyacrylate (Cosmedia SP from Cognis), Acrylates copolymer (Carbopol Aqua SF-1 from Noveon Inc.), Acrylates/acrylamides Coplymer (Noveon EC-1 from Noveon Inc.) |
| RM 19 | Hydroxyethyl/Acrylate/Sodium Acryloyldimethyl Taurate copolymer (Simulgel NS or EG from Seppic); combination with Tinosorb M claimed in PCA N°161 November 2001 |
| RM 20 | Ammonium Polyacrylates (Simulgel A from Seppic) |

"Hydro Swelling Droplets" concept

| | |
|---|---|
| RM 21 | - Glyceryl Polyacrylates (e.g., Hispagel 100) or Polymethacrylates (e.g., Lubrajel range from ISP Corp.) |
| RM 22 | Poly(Acrylamide) PAAm and its copolymers; copolymers of ammonium acrylate and acrylamide; copolymers of AAam with long hydrophobic chain and acrylates |
| RM 23 | Poly(Ethylene oxide) PEO and Poly (Propylene oxide) PPO and their copolymers; these are block terpolymers of EO and PO with the structure ABA or BAB; A: PEO with good water solubility B: PPO with limited water solubility |
| RM 2 | Poly(VinylPyrrolidone)PVP homopoplymers or Poly(VinylPyrrolidone)/Vinyl Acetate coplymers |
| RM 25 | Poly (vinylalcohol) PVA |
| RM 26 | VA/Crotonates copolymer Poly(vinylacetate)/Crotonic acid or VA/Crotonates/Vinyl Neodecanoate copolymer |
| RM 27 | Ethylene/VinylAcetate copolymer such as A.C.coplymer400 (Allied-Signal) |
| RM 28 | PVM/MA copolymers and their esterified derivatives such Ethyl, Isopropyl or Butyl esters |
| RM 29 | PVM/MA Decadiene Crosspolymer; copolymer of methyl vinyl ether/ Maleic Anhydric (PVM/MA) crosslinked with 1,9-decadiene |
| RM 30 | Polyethylene resins such as PEG-2M to PEG-9M (RITA Corp.) |
| RM 31 | polysiloxanes and copolymers; copolymers of polysiloxanes and other blocks such as PEO blocks |
| RM 32 | PEG-modified materials, the most commonly used class of non ionic thickeners with the following basic structure: $R(OCH_2CH_2)_n$ OH, werein R is the fatty moiety, like fatty alcohol, glyceryl ester, propylene glycol ester or carboxylic acid; for example; PEG-150 Distearate; these thickeners are not susceptible to hydrolysis and offer better viscosity stability under a broad range of pH and temperature profiles |
| RM 33 | Trihydroxystearin or Glycol Tri-(12-Hydroxystearate) |
| RM 34 | Glyceryl Tribehenate such as Syncrowax HRS-C from Croda |

TABLE 4

Phospholipid derivatives

RM 35  Alkylated Phosphatidyl Choline forming fluid lamellar assembly as the stable liquid crystalline phase of general formula:

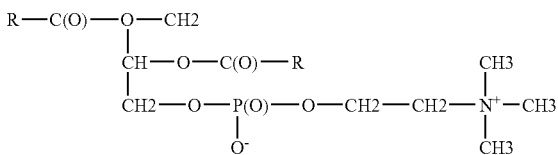

wherein R is $C_2$-$C_4$alkyl

RM 36  Phosphobetaines (amphoteric ingredients); alkylamido Phosphobetaine of general formula

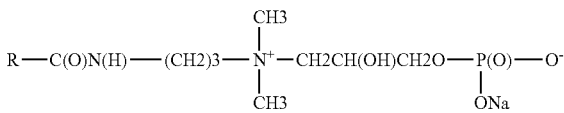

wherein R is $C_2$-$C_{14}$alkyl

RM 37  Alkyl Phosphate Quaternary compounds of general formula

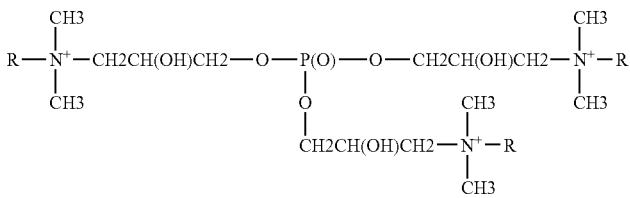

wherein R is $C_2$-$C_{14}$alkyl

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quarternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate tertbutylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5$ $Cl\times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, *costus*, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colorants

There may be used as colorants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

The following examples are given to provide a non limiting illustration of the present invention.

EXAMPLE 1

Preparation of 2(S)-[(2,3-dihydroxy-propyl)-(4-methoxy-benzenesulfonyl)amino]-N-hydroxy-acetamide [compound of formula (I) wherein $R_1$ is $CH_2$—CHOH—$CH_2OH$, $R_2$ is H and $R_3$ is $OCH_3$]

To a cold (0° C.) a suspension of H-Gly-OMe.HCl in $CH_2Cl_2$ (0.8 M) was added $Et_3N$ (3.0 eq.) and after 30 min 4-methoxybenzenesulfonyl chloride (1.0 eq.) and DMAP (0.05 eq.). The reaction mixture was stirred at room temperature for 24 h and then was quenched neutralizing with 3% HCl in $H_2O$. The organic layer was extracted with $CH_2Cl_2$ and was dried over $Na_2SO_4$. The solvent was evaporated and the residue purified by crystallization. White solid (yield=93%).

The product was dissolved in dimethylformamide (DMF). The solution was cooled to 0° C. and was added NaH (1.1 eq.). The reaction mixture was warmed to room temperature and added with the iodine derivative of (S)-(+)-2,2-dimethyl-1,3-dioxolane-4-methanol, previously prepared according to standard procedure commonly used and well known to any skilled person. The reaction was stirred at room temperature for 20 h and was quenched neutralizing with a saturated aqueous $NH_4Cl$ solution. The organic layer was extracted with $CH_2Cl_2$ and was dried over $Na_2SO_4$. The solvent was evaporated and the residue purified by flash chromatography on silica gel (yield=10-30%).

The product so obtained was reacted with Amberlite® $H^+$ in MeOH to obtain the corresponding derivative deprotected from isopropylidene (yield=90%).

The product was dissolved at room temperature in a suspension of $NH_2OH.HCl$ (4 eq.) and KOH (5.0 eq.) in MeOH. After 12 h the reaction mixture was quenched by evaporation of the solvent. The residue was dissolved in ethyl acetate and the solution was neutralized with 50% acetic acid in $H_2O$.

The organic layer was extracted with ethyl acetate, dried over $Na_2SO_4$, and the solvent was evaporated. The residue was purified by flash chromatography on silica gel (yield=50%).

$^1$H-NMR (200 MHz, $CDCl_3$): δ (ppm) 3.31 (d, 2H), 3.50 (m, 1H), 3.62 (d, 2H), 3.68 (s, 3H, OMe), 4.08 (s, 2H, $CH_2$ at position α with respect to carbonyl group), 7.05 (dd, 1H, J=8.3 Hz, J'=6.2 Hz), 7.12 (dd, 1H, J=8.4 Hz, J'=6.2 Hz), 7.81 (dd, 1H, J=8.2 Hz, J'=6.0 Hz), 7.84 (dd, 1H, J=8.2 Hz, J'=6.0 Hz)).

EXAMPLE 2

Preparation of 2(R)-[(2,3-dihydroxy-propyl)-(4-methoxy-benzenesulfonyl)amino]-N-hydroxy-acetamide [compound of formula (I) wherein $R_1$ is $CH_2$—CHOH—$CH_2OH$, $R_2$ is H and $R_3$ is $OCH_3$]

The same procedure described above in Example 1 was carried out, with the only difference that iodine derivative of (S)-(+)-2,2-dimethyl-1,3-dioxolane-4-methanol was replaced by the corresponding (R) isomer, thus obtaining the title compound with the same yield as in Example 1.

$^1$H-NMR (200 MHz, $CDCl_3$): δ (ppm) 3.31 (d, 2H), 3.50 (m, 1H), 3.62 (d, 2H), 3.68 (s, 3H, OMe), 4.08 (s, 2H, $CH_2$ at position α with respect to carbonyl group), 7.05 (dd, 1H, J=8.3 Hz, J'=6.2 Hz), 7.12 (dd, 1H, J=8.4 Hz, J'=6.2 Hz), 7.81 (dd, 1H, J=8.2 Hz, J'=6.0 Hz), 7.84 (dd, 1H, J=8.2 Hz, J'=6.0 Hz)).

EXAMPLE 3

Preparation of 2-[4-methoxy-benzenesulfonyl)amino]-3,N-dihydroxy-propionamide [compound of formula (I) wherein $R_1$ is H, $R_2$ is $CH_2OH$ and $R_3$ is $OCH_3$]

To a cold (0° C.) a suspension of D-H-Ser-OMe.HCl in $CH_2Cl_2$ (0.3 M) was added $Et_3N$ (3.0 eq.) and after 30 min. 4-methoxybenzenesulfonyl chloride (1.0 eq.) and DMAP (0.05 eq.). The reaction mixture was stirred at room temperature for 20 h and then was quenched neutralizing with 3% HCl in $H_2O$. The organic layer was extracted with $CH_2Cl_2$ and was dried over $Na_2SO_4$. The solvent was evaporated and the residue purified by crystallization. White solid (yield=90%). The product was dissolved at room temperature in a suspension of $NH_2OH.HCl$ (4 eq.) and KOH (5.0 eq.) in MeOH. After 12 h the reaction mixture was quenched by evaporation of the solvent. The residue was dissolved in ethyl acetate and the solution was neutralized with 50% acetic acid in $H_2O$.

The organic layer was extracted with ethyl acetate, dried over $Na_2SO_4$, and the solvent was evaporated. The residue was purified by flash chromatography on silica gel (yield=45%).

$^1$H-NMR (200 MHz, $CDCl_3$): δ (ppm) 3.65 (d, 1H, CH at position α with respect to carbonyl group), 3.68 (s, 3H, OMe), 4.05 (d, 2H), 7.08 (dd, 1H, J=8.3 Hz, J'=6.2 Hz), 7.14 (dd, 1H, J=8.4 Hz, J'=6.2 Hz), 7.73 (dd, 1H, J=8.2 Hz, J'=6.1 Hz), 7.78 (dd, 1H, J=8.0 Hz, J'=6.2 Hz).

EXAMPLE 4

Preparation of 2-[(2,3-dihydroxy-propyl)-(4-methoxy-benzenesulfonyl)amino]-N-hydroxy-propionamide [compound of formula (I) wherein $R_1$ is $CH_2$—CHOH—$CH_2OH$, $R_2$ is $CH_2OH$ and $R_3$ is $OCH_3$]

To a cold (0° C.) a suspension of D-H-Ser-OMe.HCl in $CH_2Cl_2$ (0.3M) was added $Et_3N$ (3.0 eq.) and after 30 min. 4-methoxybenzenesulfonyl chloride (1.0 eq.) and DMAP (0.05 eq.). The reaction mixture was stirred at room temperature for 20 h and then was quenched neutralizing with 3% HCl in $H_2O$. The organic layer was extracted with $CH_2Cl_2$ and was dried over $Na_2SO_4$. The solvent was evaporated and the residue purified by crystallization. White solid (yield=90%).

The hydroxyl of serine was protected by selective acetylation according to standard procedure. The product was dissolved in DMF. The solution was cooled to 0° C. and was added NaH (1.1 eq.). The reaction mixture was warmed to room temperature and added with the iodine derivative of (S)-(+)-2,2-2,2-dimethyl-1,3-dioxolane-4-methanol, previously prepared according to the standard procedure commonly used and well known to any skilled person. The reaction was stirred at room temperature for 20 h and was quenched neutralizing with a saturated aqueous $NH_4Cl$ solution.

The organic layer was extracted with $CH_2Cl_2$ and was dried over $Na_2SO_4$. The solvent was evaporated and the residue purified by flash chromatography on silica gel (yield=10-30%).

The hydroxyl groups were deprotected from isopropylidene group with Amberlite® $H^+$ in MeOH, then the mixture is treated with NaOMe/MeOH and brought to neutral pH.

The so obtained product was dissolved in a suspension of $NH_2OH.HCl$ (4 eq.) and KOH (5.0 eq.) in MeOH. After 24 h the reaction mixture was quenched by neutralization with acetic acid and evaporation of the solvent. The residue was purified by chromatography on silica gel.

$^1$H-NMR (200 MHz, CDCl$_3$): δ (ppm) 3.28 (d, 2H), 3.54 (m, 1H), 3.65 (d, 1H), 3.68 (d, 2H), 3.71 (s, 3H, OMe), 3.90 (d, 2H), 7.08 (dd, 1H, J=8.3 Hz, J'=6.2 Hz), 7.10 (dd, 1H, J=8.4 Hz, J'=6.2 Hz), 7.76 (dd, 1H, J=8.2 Hz, J'=6.1 Hz), 7.82 (dd, 1H, J=8.0 Hz, J'=6.2 Hz).

EXAMPLE 5

Preparation of N-hydroxy-2-[(4-methoxy-benzenesulfonyl)-(2-(3,4,5-trihydroxy-6-hydroxymethyl-tetrahydro-pyran-2-yl-oxy)-ethyl]-acetamide [Compound of Formula (I) wherein $R_1$ is $CH_2$—$CH_2$—O-glucose, $R_2$ is H and $R_3$ is $OCH_3$]

To a cold (0° C.) a suspension of H-Gly-OMe.HCl in $CH_2Cl_2$ (0.8 M) was added $Et_3N$ (3.0 eq.) and after 30 min 4-methoxybenzenesulfonyl chloride (1.0 eq.) and 4-dimethylaminopyridine (0.05 eq.). The reaction mixture was stirred at room temperature for 24 h and then was quenched neutralizing with 3% HCl in $H_2O$. The organic layer was extracted with $CH_2Cl_2$ and was dried over $Na_2SO_4$. The solvent was evaporated and the residue purified by crystallization. White solid (yield=93%).

The product was dissolved in DMF. The solution was cooled to 0° C. and was added NaH (1.1 eq.). The reaction mixture was warmed to room temperature and was added 1-acetyl-2-bromoethanol (1.0 eq.). The reaction was stirred at room temperature for 20 h and was quenched neutralizing with a saturated aqueous $NH_4Cl$ solution. The organic layer was extracted with $CH_2Cl_2$ and was dried over $Na_2SO_4$. The solvent was evaporated and the residue purified by flash chromatography on silica gel (yield=65%).

The hydroxyl group was deprotected according to standard procedure by treatment with NaOMe/MeOH.

The product obtained was dissolved in $CH_2Cl_2$. The solution was added with 1-bromo-tetra-acetylglucose (1.0 eq.) and cooled to −40° C. The reaction mixture was added with silver triflate (1.0 eq.) and warmed to room temperature. After 2 h the reaction was quenched neutralizing with saturated aqueous $NaHCO_3$ solution. The organic layer was extracted with $CH_2Cl_2$ and was dried over $Na_2SO_4$. The solvent was evaporated and the residue purified by flash chromatography on silica gel (yield=50%). The product was completely deacetylated with NaOMe/MeOH.

The so obtained product was dissolved in a suspension of $NH_2OH.HCl$ (4 eq.) and KOH (5.0 eq.) in MeOH. After 24 h the reaction mixture was quenched by naturalization with acetic acid and evaporation of the solvent. The residue was purified by flash chromatography on silica gel.

The so obtained product was analysed by ESI-MS: m/z [466] $M^+$

EXAMPLE 6

Preparation 2-[(2,3-dihydroxy-propyl)-(4-biphenyl-sulfonyl)amino]-N-hydroxy-acetamide [compound of formula (I) wherein $R_1$ is $CH_2$—CHOH—$CH_2OH$, $R_2$ is H and $R_3$ is phenyl]

The title compound was prepared as described above in the Example 1, with the only difference that 4-biphenylsulfonyl chloride was used instead of 4-methoxybenzenesulfonyl chloride.

On the product thus obtained, $^1$H-NMR and $^{13}$C-NMR spectroscopic analyses were carried out, and the following results were obtained:

$^1$H-NMR (200 MHz, CD$_3$OD): δ (ppm) 3.18 (dd, 1H), 3.45 (dd, 1H), 3.55 (m, 1H), 3.81 (dd, 2H), 4.05 (s, 2H, $CH_2$ at position α with respect to carbonyl group), 7.22 (dd, 1H, J=8.2 Hz, J'=6.4 Hz), 7.34 (dq, 2H, J=8.1 Hz, J'=6.5 Hz), 7.48 (dd, 2H, J=8.4 Hz, J'=6.2 Hz), 7.76 (d, 2H, J=8.0 Hz), 7.94 (d, 2H, J=8.2 Hz).

EXAMPLE 7 (COMPARISON)

Preparation of 3,N-dihydroxy-2-[(4-methoxy-benzenesulfonyl)amino]-propionamide [compound of formula (I) wherein $R_1$ is $CH_2$—$CH_2$—OH, $R_2$ is H and $R_3$ is $OCH_3$]

The compound was prepared as described above in the Example 1, with the difference that 1-acetyl-2-bromoethanol was used instead of 2,2-dimethyl-1,3-dioxolane-4-methanol.

EXAMPLE 8

In Vitro Inhibition Test

The compounds of the invention, prepared as above described, were tested in vitro according to the method reported by Knight et al. in *FEBS Lett* 1992, 296 (3):263.

Catalytic domain of MMP-12 was cloned, expressed and purified according to the procedure reported in Banci et al.

*Journal of Molecular Catalysis A: Chemical,* 2003, Vol. 204-205, pp. 401-408). Preparation of catalytic domain of MMP-1 was performed as follows: proMMP-1 cDNA was cloned into the pET21 (Novagen) expression vector. The recombinant vector was transformed into *Escherichia Coli* BL21 cells. The bacteria were grown in 2 XYt media and incubated at 37° C. When the cells reached the exponential growth phase, the expression of the protein was induced by adding 0.5 mM of IPTG and the incubation was continued further for four hours. The MMP-1 catalytic domain precipitated in the inclusion bodies and these were solubilized, after lysis of the cells, in a solution of 2 M urea and 20 mM Tris-HCl pH 8. The protein was purified by using a Hiprep 16/10 (20 mL) Q FF (Pharmacia) with a linear gradient of NaCl up to 0.5 M. The purified protein was then refolded by using a multi step dialysis against solutions containing 50 mM Tris-HCl pH 7.2; 10 mM $CaCl_2$; 0.1 mM $ZnCl_2$; 0.3 M NaCl. Then the protein is activated by reacting for 12 h in presence of 1 M 4-phenylmercuric acetate. The 4-phenylmercuric acetate was then removed by dialysis against a solution containing 10 mM Tris-HCl pH 7.2; 5 mM $CaCl_2$, 0.1 mM $ZnCl_2$; 0.3 M NaCl.

To assess the enzymatic activity of the protein expressed and to test compounds of formula (I) of the invention the following polypeptide was used:

Mca-Pro-Leu-Gly-Leu-Dpa-Ala-Arg-$NH_2$ AcOH

[Mca=(7-methoxy-coumarin-4-yl)acetyl; Dpa=N-3-(2,4-dinitrophenyl)-L-, -diaminopropionyl].

This substrate whose code is P-126, is a commercially available product by BIOMOL International I.p.

Tests were performed in a buffer containing HEPES 50 mM, $CaCl_2$ 10 mM, Brij-35 0.05%, pH 7.

The compounds prepared as above, were solubilized in dimethyl sulfoxide (DMSO) and the so obtained solution was subsequently diluted with buffer so as to reach 1% DMSO inside the cell.

Experiments were carried out at 298 K by incubating the solutions at this temperature and by using a thermostatic system for the cell (Peltier). A solution DMSO/buffer in the same ratio was used as control.

The protein was maintained in presence of inhibitor for 5 min before the substrate was added. Subsequently, after addition of peptidic substrate, the increase of fluorescence intensity was measured vs. time (excitation 328 nm, emission 393 nm) using a Varian/Eclipse fluorimeter.

Matrix metalloproteinases cleave peptidic bond glycine-leucine separating coumarinic group from 2,4-dinitrophenol and so causing a high increase of fluorescence intensity under the conditions indicated above.

Starting from concentration zero (absence of the inhibitor), subsequent measurements were carried out increasing the concentration of tested compound in the sample. The fitting of rates as a function of the inhibitor concentration provided the $IC_{50}$ value for each compound.

The so obtained experimental data showed the high ability of compounds of the invention to inhibit MMP-12, MMP-8 and MMP-13, and their selectivity toward this metalloproteinase, especially compared to the inhibition activity toward MMP-7. The present compounds show therefore an ideal therapeutic and pharmacological profile, in particular for the treatment of pathologic conditions where MMP-12 is involved, such as pulmonary emphysema, and where MMP-8 and MMP-13 are involved, such as periodontitis.

Moreover, the present compounds of formula (I) showed to be capable to sufficiently inhibit MMP-1 too, thus suggesting their use in anti-ageing cosmetic preparations.

Moreover, their good solubility in water improves the bioavailability of active principle and allows preparing stable aqueous aerosol formulations, particularly suitable for the treatment of pulmonary pathologies, such as emphysema.

The $IC_{50}$ value obtained for comparison compound of Example 7 showed that compounds analogue to compounds of formula (I) and having good solubility thanks to the hydroxyl group in $R_1$ radical, do not have the inhibition activity and selectivity of present compounds of formula (I), in which $R_1$ radical comprises at least two hydroxyl groups.

The invention claimed is:

1. Compounds of formula (I)

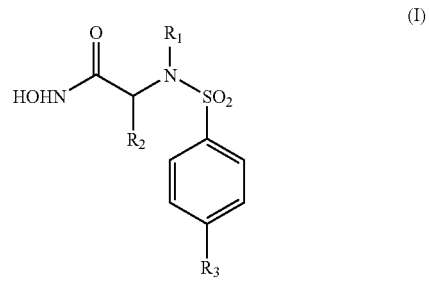

wherein
$R_1$ is 2,3-dihydroxy-propyl,
$R_2$ is selected from the group consisting of H, alkyl optionally substituted with one or more hydroxyl groups, aryl, and lateral chains of amino acids,
$R_3$ is selected from the group consisting of H, OH, alkyl, aryl, oxoalkyl, and oxoaryl, and pharmaceutically acceptable salts thereof.

2. Compounds of formula (I) according to claim 1, selected from the group consisting of the following compounds:
2(S)-[(2,3-dihydroxy-propyl)-(4-methoxy-benzenesulfonyl)amino]-N-hydroxy- acetamide;
2(R)-[(2,3-dihydroxy-propyl)-(4-methoxy-benzenesulfonyl)amino]-N-hydroxy- acetamide;
2-[(2,3-dihydroxy-propyl)-(4-methoxy-benzenesulfonyl)amino]-N-hydroxy- propionamide; and
2-[(2,3-dihydroxy-propyl)-(4-biphenylsulfonyl)amino]-N-hydroxy-acetamide.

3. Pharmaceutical compositions comprising at least a compound of formula (I) as defined in claim 1 as the active principle.

4. Pharmaceutical compositions according to claim 3, further comprising pharmaceutically acceptable excipients and/or diluents.

5. Cosmetic preparations comprising at least a compound of formula (I) as defined in claim 1 as the active principle.

6. Cosmetic preparations according to claim 5, further comprising cosmetically acceptable excipients and adjuvants.

* * * * *